(12) United States Patent
Nishizaki et al.

(10) Patent No.: US 6,475,801 B1
(45) Date of Patent: Nov. 5, 2002

(54) ANTICOAGULANT AND HEMANALYSIS METHOD

(75) Inventors: Mikiko Nishizaki, Kobe; Yasumasa Akai, Ono; Sayaka Nakamura, Ishigaki, all of (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/385,249

(22) Filed: May 12, 2000

(30) Foreign Application Priority Data

Sep. 3, 1998 (JP) .......................................... 10-249265

(51) Int. Cl.$^7$ ............................................... G01N 33/86
(52) U.S. Cl. ............................... 436/69; 436/8; 436/18; 435/2; 435/13; 73/64.41; 600/369
(58) Field of Search .............................. 436/8, 10, 18, 436/63, 69, 176; 252/408.1; 435/2, 13; 73/64.41; 600/368, 369

(56) References Cited

U.S. PATENT DOCUMENTS 4,994,367 A * 2/1991 Bode et al. .................... 435/2
5,187,102 A   2/1993 Stocker ........................ 436/69

OTHER PUBLICATIONS

Ray et al. *Blood Coagulation and Fibrinolysis*, vol. 4, pp. 805–807, 1993.*
Reinhart et al. *Journal of Laboratory & Clinical Medicine*, vol. 115, No. 1, pp. 98–103, Jan. 1990.*
Caterina et al. *American Journal of Clinical Pathology*, vol. 99, No. 2, pp. 163–167, Feb. 1993.*
Brown, *Hematology:Principles and Procedures*. 3rd Edition, p. 8, 1980.*
Haematologica, vol. 78, No. 6, 1993, pp. 364–370.
Am J. Hematol., 50(1), pp. 40–45, 1995.
Thromb. Haemostasis, 61(3), pp. 511–516, 1989.
Thromb. Haemostasis, 57(2), pp. 226–231, 1987.
Thrombosis Research, vol. 31, No. 2, pp. 365–374, 1983.
Journal of Laboratory and Clinical Medicine, vol. 111, No. 1, pp. 118–124, 1988.
Journal of Laboratory and Clinical Medicine, vol. 113, No. 6, pp. 753–758, 1989.

* cited by examiner

*Primary Examiner*—Maureen M. Wallenhorst
(74) *Attorney, Agent, or Firm*—Cohen, Pontani, Lieberman & Pavane (57) ABSTRACT

An anticoagulant for blood cell counting containing at least two kinds of the following antiplatelet agents: theophyllines, adenosines and dipyridamoles. The anticoagulant also contains citric acid, an alkali metal salt thereof or a mixture of citric acid and an alkali metal salt thereof.

1 Claim, 10 Drawing Sheets

ANTICOAGULANT AND HEMANALYSIS METHOD

CROSS-REFERENCE TO RELATED APPLICATION

This application is related to Japanese application No. 10(1998)-249265 filed on Sep. 3, 1998, whose priority is claimed under 35 USC §119, the disclosure of which is incorporated by reference in its entirety.

BACKGROUND OF THE INVENTION

1. Field of the Invention

The present invention relates to an anticoagulant and a hemanalysis method, more particularly to an anticoagulant using an antiplatelet agent cocktail and a hemanalysis method using such an anticoagulant.

2. Description of Related Art

Currently, in blood test, an appropriate anticoagulant is selected for use among a variety of anticoagulants depending upon the purpose and type of tests. For example, EDTA salts are often used for blood cell count tests, and citrates are generally used for blood coagulation tests. For biochemical tests, anticoagulants are not used or heparin is used.

Such selection of anticoagulants for use is necessary because determination of test items may be affected by use of an anticoagulant. For example, if an EDTA salt is used for a coagulation test, coagulation time cannot be determined or may be prolonged. On the other hand, use of a citrate for a blood cell count test results in a decrease in the number of platelets because platelets aggregate, and therefore the number of leukocytes increases seemingly. Thus, unless a proper anticoagulant is selected and used depending upon the purpose and type of tests, correct results cannot be obtained from the test, which can lead to a misdiagnosis.

Further, it is known that, even if an EDTA salt is used, agglutination of platelets occurs in some particular samples and thereby a pseudo decrease of platelets takes place. The pseudo decrease means a seeming decrease in the number of platelets. Thus the EDTA salts are not always free from problems in blood cell count tests.

Usually, when blood is analyzed, blood sample of a patient is often taken at once and put in a number of test tubes for blood sampling (about 2 ml to about 5 ml per tube) which contain different anticoagulants. However, this means that a relatively large amount of blood and accordingly much effort are required. Therefore, a burden is imposed on the patient whose blood sample is being taken.

Also the need to prepare test tubes containing different anticoagulants for individual test items raises costs of hemanalysis. Furthermore, an increase in the number of test tubes may enlarge the possibility that test tubes containing blood samples are mistaken for each other.

Accordingly, there is a demand for an anticoagulant which allows a plurality of blood tests to be conducted with one test tube.

SUMMARY OF THE INVENTION

The inventors of the present invention have been made an earnest study on anticoagulants for the purpose of providing a simple hemanalysis method and reducing burdens on patients, in other words, for the purpose of providing an anticoagulant and a hemanalysis method which allow both blood cell count tests and coagulation tests or both blood cell count tests and biochemical tests to be carried out on the same blood sample. The inventors of the present invention have tried diverting a so-called CTAD (containing antiplatelet agents of theophylline, adenosine and dipyrldamole as well as citric acid or alkali metal salt thereof and generally used as an anticoagulant for determining activation of platelets, for monitoring a heparin therapy and the like) to leukocyte and erythrocyte counting, which is a quite different use from what the CTAD is conventionally used for. Unexpectedly, it has been found that the leukocyte and erythrocyte counting can be done without adverse effects which were usually expected to be caused by use of the CTAD. Further, it has been found that both blood cell count tests and coagulation tests can be performed with use of the CTAD. Thus the present invention has been achieved.

Also, the inventors have found that both blood cell count tests and biochemical tests can be performed with use of a thrombin inhibitor together with the above-mentioned antiplatelet agents, finally to achieve the present invention.

The present invention provides an anticoagulant for blood cell counting comprising at least two kinds of antiplatelet agents selected from the group consisting of three kinds of antiplatelet agents which are theophyllines (T), adenosines (A) and dipyridamoles (D), and citric acid, an alkali metal salt thereof or a combination of citric acid and an alkali metal salt thereof (C) (also referred to as a citric acid-base anticoagulant hereinafter).

In another aspect, the present invention provides a hemanalysis method comprising adding the above-described anticoagulant for blood cell counting to a blood sample and counting at least two kinds of blood cells selected from the group consisting of leukocytes, erythrocytes and platelets in the blood sample.

In still another aspect, the present invention provides an anticoagulant for blood cell counting comprising at least two kinds of antiplatelet agents selected from the group consisting of three kinds of antiplatelet agents which are theophyllines, adenosines and dipyridamoles, and a thrombin inhibitor.

Further, the present invention provides a hemanalysis method comprising adding this anti-coagulant for blood cell counting to a blood sample and counting at least two kinds of blood cells selected from the group consisting of leukocytes, erythrocytes and platelets in the blood sample.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 3($a$) to 3($c$) are graphical representations showing the results of biochemical tests in the case where heparin is used as a thrombin inhibitor of the present invention, as compared with a control;

FIGS. 4(a) to 4(c) are graphical representations showing the results of biochemical tests in the case where heparin is used as a thrombin inhibitor of the present invention, as compared with a control;

FIGS. 5(a) to 5(c) are graphical representations showing the results of biochemical tests in the case where heparin is used as a thrombin inhibitor of the present invention, as compared with a control;

FIGS. 6(a) to 6(c) are graphical representations showing the results of biochemical tests in the case where chondroitin sulfate is used as a thrombin inhibitor of the present invention, as compared with a control;

FIGS. 7(a) to 7(c) are graphical representations showing the results of biochemical tests in the case where chondroitin sulfate is used as a thrombin inhibitor of the present invention, as compared with a control;

FIGS. 8(a) to 8(c) are graphical representations showing the results of biochemical tests in the case where chondroitin sulfate is used as a thrombin inhibitor of the present invention, as compared with a control;

FIGS. 9(a) to 9(c) are graphical representations showing the results of biochemical tests in the case where chondroitin sulfate is used as a thrombin inhibitor of the present invention, as compared with a control;

FIGS. 10(a) to 10(c) are graphical representations showing the results of biochemical tests in the case where chondroitin sulfate is used as a thrombin inhibitor of the present invention, as compared with a control;

DESCRIPTION OF THE PREFERRED EMBODIMENTS

The anticoagulant of the present invention mainly contains at least two kinds of antiplatelet agents selected from the group consisting of three kinds of antiplatelet agents which are theophyllines, adenosines and dipyridamoles, as well as citric acid, an alkali metal salt thereof or a combination of citric acid and an alkali metal salt thereof, or otherwise the anticoagulant comprises the above-mentioned at least two kinds of antiplatelet agents and a thrombin inhibitor.

Here, as alkali metal salts of citric acid usable for the anticoagulant of the present invention, sodium salts, potassium salts and the like may be mentioned. Among these alkali metal salts, the sodium salt is preferable.

As theophyllines, compounds represented by the following formula:

(wherein $R^1$ is a lower alkyl group), hydrates thereof, salts thereof (e.g., sodium salts, sodium acetate salts, salts with ethylenediamine, ethanolamine, isopropanolamine, etc.) and esters thereof may be mentioned.

Here, examples of the lower alkyl groups include $C_{1-3}$ alkyl groups such as methyl, ethyl and propyl. Among such theophyllines, theophylline whose $R^1$ is methyl is preferable.

As adenosines, compounds represented by the following formula:
(wherein $R^2$ is a lower alkylene group), hydrates thereof, salts thereof (e.g., diphosphates, triphosphates, tetraphosphates, etc.) and esters thereof may be mentioned.

Here, examples of the lower alkylene groups include $C_{1-3}$ alkylene groups such as methylene, ethylene and propylene. Among such adenosines, adenosine whose $R^2$ is methylene is preferable.

As dipyridamoles, compounds represented by the following formula:

(wherein $R^3$ is an alkylene group), hydrates thereof, salts thereof (e.g., sodium salts, etc.) and esters thereof may be mentioned.

Here, examples of the alkylene groups include $C_{1-6}$ alkylene groups such as methylene, ethylene, propylene, n-butylene, t-butylene, n-heptylene and n-hexylene. Among such dipyridamoles, dipyridamole whose $R^3$ is ethylene is preferable.

As the thrombin inhibitor, any one that is known in the field of art may be used. Examples thereof include heparin (H), chondroitin sulfate (Cd) and salts thereof (e.g., sodium salts, potassium salts, salts with amines, etc.).

The anticoagulant of the present invention contains at least two kinds of antiplatelet agents selected from the three kinds of antiplatelet agents which are theophyllines (T), adenosines (A) and dipyridamoles (D). That is, the anticoagulant may contain at least one compound of the theophyllines and at least one compound of the adenosines, or at least one compound of the theophyllines and at least one compound of the dipyridamoles, or at least one compound of the adenosines and at least one compound of the dipyridamoles. However, an anticoagulant containing three kinds of antiplatelet agents, i.e., at least one compound of the theophyllines, at least one compound of the adenosines and at least one compound of the dipyridamoles, is preferable. An anticoagulant containing theophylline, adenosine and dipyridamole is more preferable. For each group of theophyllines (T), adenosines (A) and dipyridamoles (D), only one compound may be selected from each group, or two or more compounds may be selected from each group to be used as a combination.

As the citric acid-base anticoagulant (C), citric acid alone or an alkali metal salt of citric acid alone may be used, or a combination of citric acid and an alkali metal salt of citric acid may be used.

In the anticoagulant of the present invention, the antiplatelet agents must be used in an amount sufficient for preventing aggregation or agglutination, deformation and adhesion of platelets in a blood sample. The citric acid-base anticoagulant must be used in an amount sufficient for preventing coagulation of a blood sample. The thrombin inhibitor must be used in an amount sufficient for preventing thrombin activity in a blood sample.

For example, the use ratio of the antiplatelet agents to the citric acid-base anticoagulant (C) may preferably be about 0.9:80 to about 90:80 (by weight), more preferably about 8:80 to about 40:80 (by weight). It is noted that in the following description, the use ratio is a ratio by weight unless otherwise indicated.

More particularly, T:A:C may be about 14:5:160, and about 1.4 mg:0.5 mg:16 mg with respect to 5 ml of blood sample; T:D:C may be about 28:1:320, and about 1.4 mg:0.05 mg:16 mg with respect to 5 ml of blood sample; A:D:C may be about 10:1:320, and about 0.5 mg:0.05 mg:16 mg with respect to 5 ml of blood sample; and with respect to 5 ml of blood sample, T:A:D:C may be about 0.3 to 15 mg:0.1 to 8 mg:0.01 to 0.7 mg:5 to 120 mg, and 15:4:0.2:100 in molar ratio.

The use ratio of the antiplatelet agents to the thrombin inhibitor may preferably be about 0.05:11 to about 4,000:11, more preferably about 0.05:11 to about 2,000:11.

More particularly, T:A:H may be about 135:50:1, and about 0.35 mg:0.5 mg:0.01 mg with respect to 5 ml of a blood sample; T:D:H may be about 135:5:1, and about 0.35 mg:0.05 mg:0.01 mg with respect to 5 ml of a blood sample; A:D:H may be about 50:5:1, and about 0.5 mg:0.05 mg:0.01 mg with respect to 5 ml of a blood sample; and with respect to 5 ml of a blood sample, T:A:D:H may be about 0.3 to 15 mg:0.1 to 8 mg:0.01 to 0.7 mg:0.01 to 0.5 mg.

Further, T:A:Cd may be about 14:5:228, and about 1.4 mg:0.5 mg:22.8 mg with respect to 5 ml of a blood sample; T:D:Cd may be about 27:1:455, and about 1.35 mg:0.05 mg:22.72 mg with respect to 5 ml of a blood sample; A:D:Cd may be about 10:1:445, and about 0.5 mg:0.05 mg:22.75 mg with respect to 5 ml of a blood sample; and with respect to 5 ml of a blood sample, T:A:D:Cd may be about 0.3 to 15 mg:0.1 to 8 mg:0.01 to 0.7 mg:0.1 to 100 mg.

In the hemanalysis method of the present invention, the aforesaid antiplatelet agents and the aforesaid citric acid-base anticoagulant or the aforesaid thrombin inhibitor are added to a blood sample. Here the blood sample means a sample of peripheral blood of a mammal, especially a human, a sample collected by apheresis, or the like. When the anticoagulant of the present invention is added to the blood sample, the components of the anticoagulant may be added thereto in an optional order, or alternatively the antiplatelet agents may be mixed with the citric acid-base anticoagulant or the thrombin inhibitor beforehand and the obtained mixture may be add to the blood sample. Further, it may be possible to dissolve the mixture in an appropriate solvent and pour the resulting mixture into test tubes or the like to be used for collecting blood samples. Subsequently, the mixture in the test tubes may be used as it is, or the mixture may be dried before blood samples are fed into the test tubes. Temperature at which the anticoagulant is mixed with the blood sample is not particularly limited, but may be around room temperature, for example.

The resulting blood sample may be used for blood cell count tests, and subsequently, plasma may be taken from the sample by centrifugation and used for coagulation tests or biochemical tests. Or the resulting blood sample may be divided into two, one of which may be subjected to the blood cell count tests and the other may be subjected to the coagulation tests or the biochemical tests. Or if the amount required for the coagulation tests or the biochemical tests is such that does not affect the blood cell count tests, the resulting blood sample may be centrifuged to take the required amount of plasma, which is subjected to the coagulation tests or the biochemical tests, and subsequently the remaining blood sample may be stirred and subjected to the blood cell count tests. Especially, it is preferable that the coagulation tests or the biochemical tests are carried out after the blood cell count tests or that the blood cell count tests are carried out separately from the coagulation tests or the biochemical tests. Suitably, the blood cell count tests, the coagulation tests and the biochemical tests are conducted around room temperature. However, temperature may be adjusted as appropriate for a testing apparatus to be used.

In the hemanalysis method of the present invention, the counting of leukocytes includes not only obtaining a whole leukocyte count but obtaining the counts of lymphocytes, monocytes, granulocytes (neutrophils, eosinophils and basophils) and the like included in the leukocytes and the ratios thereof.

Also, the counting of erythrocytes includes not only obtaining an erythrocyte count but obtaining a hemoglobin concentration, a hematocrit, erythrocyte indices calculated from such data (mean corpuscular volume (MCV), mean corpuscular hemoglobin (MCH) and mean corpuscular hemoglobin concentration (MCHC)), the count and ratio of reticulocytes and the like.

Further, the counting of platelets includes not only obtaining a platelet count but obtaining a mean platelet volume and the ratio of large platelets.

The blood cell countings may be conducted by a manual microscopic method or by use of a blood cell counter. There are blood cell counters of an electric resistance type, an optical type and the like. Any type of counter may be used.

The coagulation tests mean determination of one or more blood coagulation test items, for example, prothrombin time (PT), activated partial thromboplastin time (APTT), fibrinogen (Fbg), the amounts of extrinsic coagulation factors (II, V, VII, X), the amount of intrinsic coagulation factors (VIII, IX, X I, X II), thrombo test (TTO), hepaplastin test (HpT), AT-III, PLG, $\alpha_2$PI, PC, FDP, D—D dimers and the like. The determination may be carried out by an appropriate method selected from known methods, such as an automated method, a PT method or APTT method by means of a human deficiency plasma correction method, an Owren plasma method, a plasma method, a latex fixation method, an SRID method and the like.

The coagulation tests may be conducted either by a manual method or by automatic determination. For automatic determination, there are a light scatter detection method which detects an increase in light scatter of plasma when fibrin forms and a physical detection method which detects a change in viscosity of plasma when a mass of fibrin forms, and the like. Any method may be used.

The biochemical tests mean tests for qualitatively and quantitatively analyzing components of blood by biochemical methods, such as a nitrogenous component test, metal test, plasma protein-related test, colloid reaction biochrome test, enzyme-related test, lipid test, electrolyte test, saccarometabolism test and the like. More particularly, the biochemical tests mean tests for determining one or more of general biochemical test items such as creatine phosphokinase (CPK), blood urea nitrogen (BUN), lactate dehydrogenase (LDH), alkaline phosphatase (ALP), GOT, GPT, triglyceride (TG), urea (UA), total cholesterol (TCHO), total proteins (TP), albumin (ALB), amylase (AMYL), γ-glutamine transpeptidase (GGT), creatine (CRE), total bilirubin (TBIL), C-reactive protein (CRP) and the like. The determination may be carried out by a method selected from known methods such as a creatine phosphate substrate· diaphorase· formazan pigment method, urease· BCG indicator method, lactic substrate· diaphorase· formazan pigment method, p-nitrophenyl phosphate substrate method, urecase· POD method, buret method, BCG indicator method and the like. The biochemical tests may be conducted either by a manual method or by automatic determination provided that these general biochemical test items can be determined.

EXAMPLES

The anticoagulant and hemanalysis method of the present invention are now described in detail by way of examples.

Example 1

CTAD

An anticoagulant was prepared so that 2.89 mg of citric acid (of analytical grade, produced by Nacarai Tesque Inc. Japan), 12.1 mg of sodium citrate (of analytical grade, produced by Nacarai Tesque Inc. Japan), 1.4 mg of theophylline (anhydrous, produced by Sigma-Aldrich Corporation, Japan), 0.49 mg of adenosine (produced by Sigma-Aldrich Corporation, Japan) and 0.05 mg of dipyridamole (produced by Sigma-Aldrich Corporation, Japan) were contained per 5-ml test tube for blood sampling.

A. Blood Cell Count Tests and Blood Coagulation Tests

Blood was collected into test tubes containing the anticoagulant (CTAD) prepared as above and subjected to blood cell count tests (leukocyte count (WBC), ratios of leukocytic components (neutrophil ratio (NEUT%), lymphocyte ratio (LYMPH%), monocyte ratio (MONO%), eosinophil ratio (EOSI%) and basophil ratio (BASO%)), erythrocyte count (RBC), hemoglobin concentration (Hgb), hematocrit (Hct), MCV, MCH, MCHC and platelet count (PLT))(used counter: SE-9000™ produced by Sysmex Corporation, Japan) and coagulation tests (prothrombin time (PT), activated partial thromboplastin time (APTT), fibrinogen determination (Fbg))(used tester:CA-1000 produced by Sysmex Corporation, Japan).

EDTA-2K (Venoject II™ or 5 ml produced by Terumo), 5 mg, was used as a control for the blood cell count tests and a 3.8% solution of sodium citrate (3.8% solution of sodium citrate for 5 ml produced by Terumo, Japan), 0.5 ml, was used as a control for the blood coagulation tests, respectively, in place of the above anticoagulant.

The tests were conducted with four normal samples, and mean values are calculated. Table 1 shows the results of the blood cell count tests and Table 2 shows the results of the blood coagulation tests.

TABLE 1

|  | CTAD | Control (EDTA-2K) |
|---|---|---|
| WBC (×10$^2$) | 58.6 | 55.9 |
| NEUT % | 61.6 | 62.9 |
| LYMPH % | 28.8 | 27.8 |
| MONO % | 4.9 | 5.0 |
| EOSI % | 4.2 | 3.8 |
| BASO % | 0.5 | 0.4 |
| RBC (×10$^4$) | 488 | 482 |
| Hgb (g/dl) | 14.9 | 14.7 |
| Hct (%) | 44.0 | 43.3 |
| MCV (fl) | 90.6 | 90.2 |
| MCH (pg) | 30.7 | 30.6 |
| MCHC (g/dl) | 33.9 | 33.9 |
| PLT (×10$^4$) | 22.9 | 22.9 |

TABLE 2

|  | CTAD | Control (sodium citrate) |
|---|---|---|
| PT (sec) | 9.3 | 9.5 |
| APTT (sec) | 27.7 | 28.6 |
| Fbg (sec) | 9.3 | 9.8 |

As shown in Tables 1 and 2, data substantially equivalent to that obtained with the controls was obtained in both the blood cell count tests and the coagulation tests.

B. Change with Time

Change with time in the blood cell counts and blood coagulation was observed using test tubes containing CTAD prepared as above. Tables 3 and 4 show the results of the blood cell counts with use of CTAD and the control, respectively.

TABLE 3

(CTAD)

|  | 0.5 hrs | 1.5 hrs | 3 hrs | 4 hrs | 8 hrs |
|---|---|---|---|---|---|
| WBC (×10$^2$) | 52.0 | 53.7 | 53.7 | 49.6 | 54.6 |
| NEUT % | 60.1 | 60.2 | 62.1 | 62.2 | 62.7 |
| LYMPH % | 30.4 | 31.0 | 31.0 | 30.5 | 29.6 |
| MONO % | 4.7 | 3.1 | 1.9 | 2.6 | 2.0 |
| EOSI % | 4.3 | 5.0 | 4.5 | 4.2 | 5.1 |
| BASO % | 0.5 | 0.7 | 0.6 | 0.6 | 0.7 |
| RBC (×10$^4$) | 537 | 523 | 525 | 524 | 525 |
| Hgb (g/dl) | 15.8 | 15.4 | 15.4 | 15.3 | 15.3 |
| Hct (%) | 46.9 | 45.7 | 45.7 | 46.1 | 46.6 |
| MCV (fl) | 87.4 | 87.2 | 87.2 | 87.9 | 88.6 |
| MCH (pg) | 29.4 | 29.4 | 29.4 | 29.2 | 29.2 |
| MCHC (g/dl) | 33.6 | 33.7 | 33.7 | 33.3 | 33.0 |
| PLT (×10$^4$) | 20.8 | 21.6 | 21.0 | 20.6 | 20.7 |

TABLE 4

(Control)

|  | 0.5 hrs | 1.5 hrs | 3 hrs | 4 hrs | 8 hrs |
|---|---|---|---|---|---|
| WBC (×10$^2$) | 54.4 | 51.9 | 51.8 | 52.3 | 51.9 |
| NEUT % | 57.1 | 56.4 | 55.7 | 56.4 | 55.4 |
| LYMPH % | 32.1 | 32.6 | 32.7 | 32.1 | 33.5 |
| MONO % | 5.9 | 5.8 | 6.0 | 6.2 | 6.0 |
| EOSI % | 4.3 | 4.6 | 4.8 | 4.6 | 4.3 |
| BASO % | 0.7 | 0.7 | 0.9 | 0.8 | 0.9 |
| RBC (×10$^4$) | 526 | 525 | 522 | 524 | 529 |
| Hgb (g/dl) | 15.5 | 15.4 | 15.4 | 15.5 | 15.6 |
| Hct (%) | 45.9 | 45.6 | 45.5 | 45.5 | 46.3 |

TABLE 4-continued (Control)

|  | 0.5 hrs | 1.5 hrs | 3 hrs | 4 hrs | 8 hrs |
|---|---|---|---|---|---|
| MCV (fl) | 87.3 | 87.0 | 87.2 | 86.9 | 87.5 |
| MCH (pg) | 29.4 | 29.7 | 29.8 | 29.7 | 29.5 |
| MCHC (g/dl) | 33.6 | 33.7 | 33.8 | 33.9 | 33.6 |
| PLT ($\times 10^4$) | 20.8 | 21.8 | 21.6 | 21.3 | 21.3 |

Tables 5 and 6 show change with time in coagulation with use of CTAD and the control, respectively.

TABLE 5

(CTAD)

|  | 1 hrs | 2 hrs | 4 hrs |
|---|---|---|---|
| PT (sec) | 9.9 | 9.9 | 9.8 |
| APTT (sec) | 31.1 | 31.0 | 30.9 |
| Fbg (sec) | 8.0 | 8.3 | 8.2 |

TABLE 6

(Control)

|  | 1 hrs | 2 hrs | 4 hrs |
|---|---|---|---|
| PT (sec) | 10.0 | 10.0 | 9.8 |
| APTT (sec) | 29.6 | 29.6 | 29.3 |
| Fbg (sec) | 8.8 | 8.8 | 8.5 |

As clearly shown in Tables 3 to 6, the anticoagulant of the present invention is equal to the controls about change with time.

C. Examination on EDTA-dependant Pseudothrombocytopenia

Figure 1:
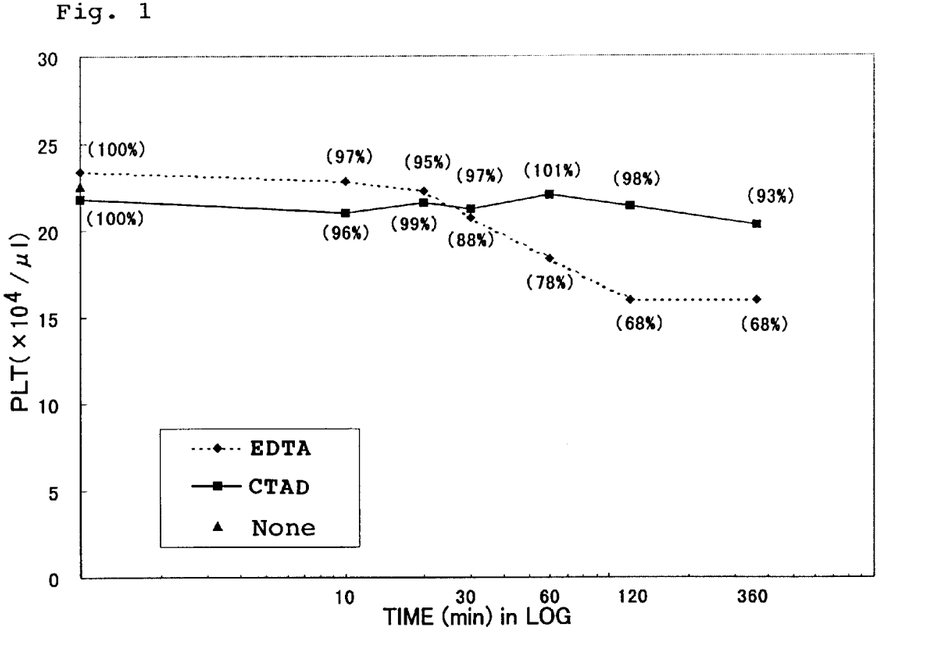
FIG. 1 is a graphical representation showing change with time in the number of platelets in samples using the anticoagulant of the present invention for examining a pseudothrombocytopenia, as compared with a control.

Blood samples to which CTAD of the present invention or EDTA-2K was added were subjected to the platelet counting in order to compare them with regard to the EDTA-dependant Pseudothrombocytopenia. The results are shown in FIG. 1.

The number of platelets decreased with time where EDTA-2k was used, while constant counting results were obtained where CTAD of the present invention was used.

D. Examination on Cold Agglutination

Blood samples to which CTAD of the present invention or EDTA-2K was added were subjected to the platelet counting in order to compare them with regard to cold agglutination (the pseudothrombocytopenia in cold storage). The samples were preserved at 4° C. and examined eight hours after collected. The results are shown in Table 7.

TABLE 7

|  | 37° C., EDTA-2K (control) | 4° C., EDTA-2K | 4° C., CTAD |
|---|---|---|---|
| PLT ($\times 10^4$) | 17.6 | 9.0 | 18.2 |

Platelets decreased where EDTA-2K was used, while the decrease of platelets was suppressed where CTAD of the present invention was used.

E. Change with Time in the Mean Platelet Volume (MPV)

Figure 2:
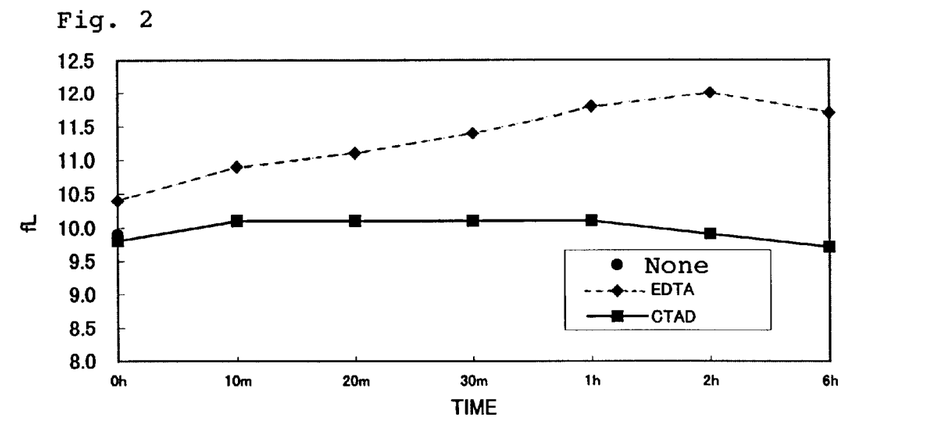
FIG. 2 is a graphical representation showing change with time in the mean platelet volume in samples using the anticoagulant of the present invention, as compared with a control.
Figure 3A:
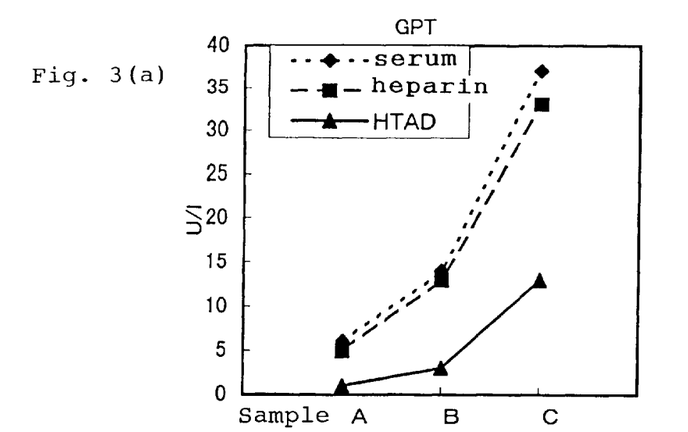
Figure 3B:
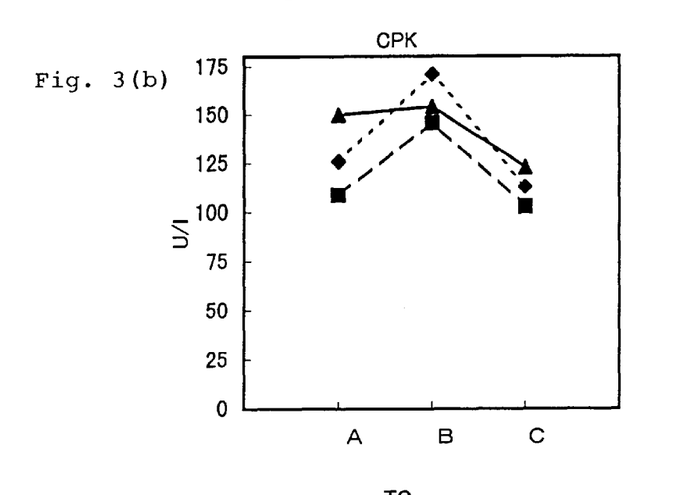
Figure 3C:
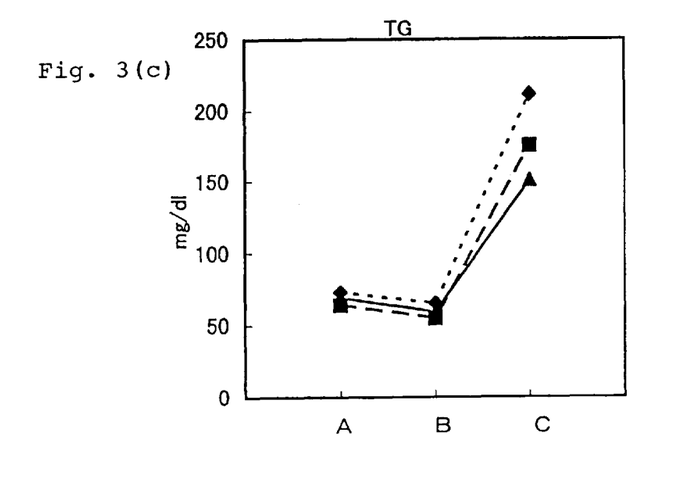
Figure 4A:
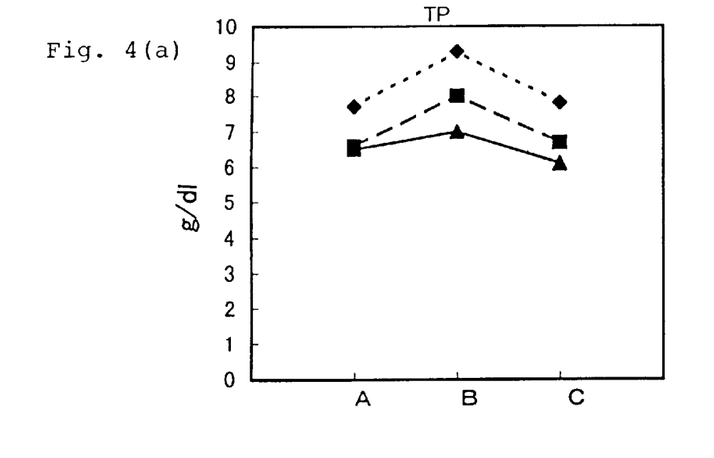
Figure 4B:
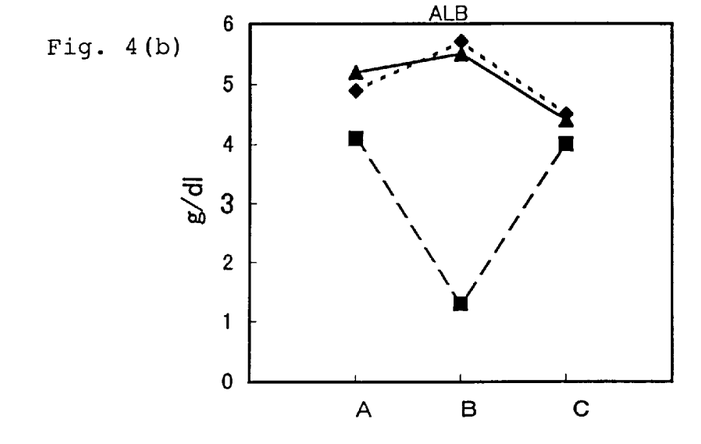
Figure 4C:
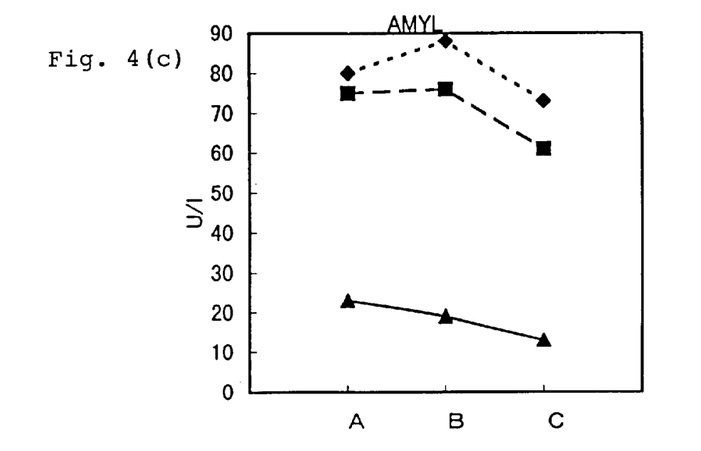
Figure 5A:
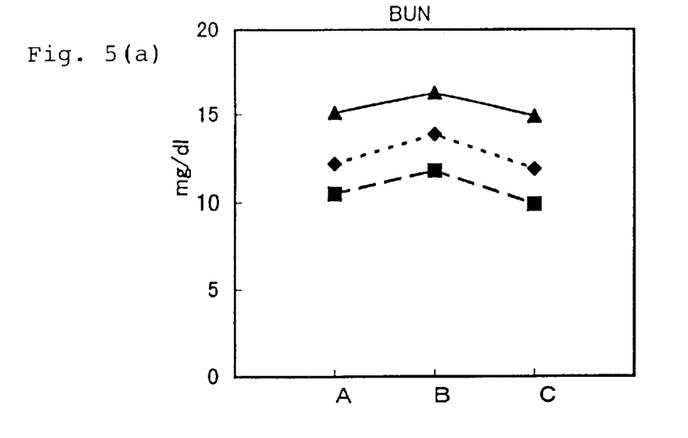
Figure 5B:
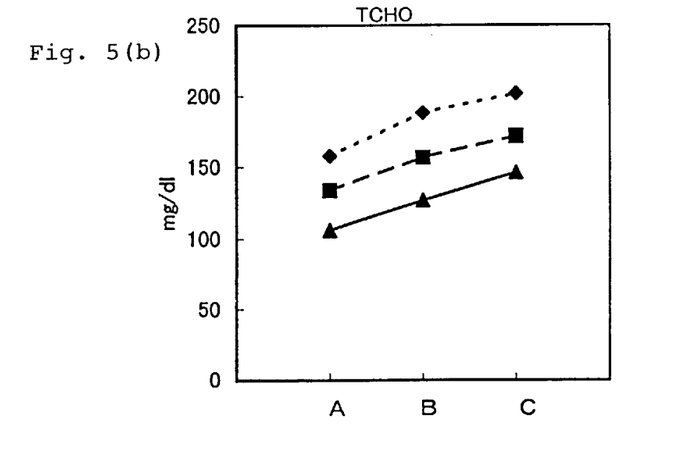
Figure 5C:
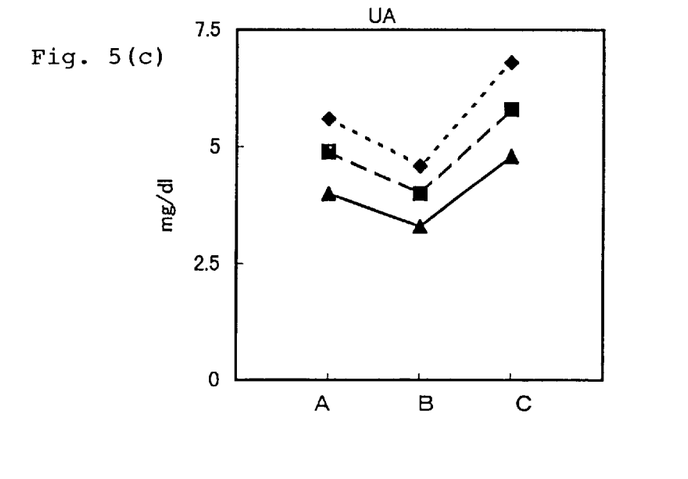

Blood samples to which CTAD of the present invention or EDTA-2K was added were compared with regard to change with time in the size of platelets. The results are shown in FIG. 2.

Platelets grew in size with time where EDTA-2K was used, while platelets maintained their inherent size (without the anticoagulant) where CTAD of the present invention was used.

Example 2

HTAD

An anticoagulant was prepared so that 0.05 mg of sodium heparin (of analytical grade, produced by Nacarai Tesque, Inc.), 14 mg of theophylline (anhydrous, produced by Sigma-Aldrich Corporation), 0.49 mg of adenosine (produced by Sigma-Aldrich Corporation) and 0.05 mg dipyridamole (produced by Sigma-Aldrich corporation) were contained per 5-ml test tube for blood sampling.

Blood Cell Count Tests and Biochemical Tests

Blood was collected into test tubes containing heparin TAD (HTAD) prepared as above and subjected to blood cell count tests after 0.5, 1, 3 and 6 hours (used counter:SE-9000™). Table 8 shows mean blood cell counts of three samples.

EDTA-2K (Venoject II™ for 5 ml produced by Terumo), 5 mg, was used as a control for the blood cell count tests. The results are shown in Table 9.

TABLE 8

(HTAD)

|  | 0.5 hrs | 1 hrs | 3 hrs | 6 hrs |
|---|---|---|---|---|
| WBC ($\times 10^2$) | 49.4 | 49.8 | 48.4 | 49.5 |
| RBC ($\times 10^4$) | 541 | 542 | 544 | 547 |
| Hgb (g/dl) | 15.8 | 15.9 | 16.0 | 16.0 |
| Hct (%) | 47.5 | 47.5 | 47.5 | 47.7 |
| MCV (fl) | 87.8 | 87.6 | 87.3 | 87.2 |
| MCH (pg) | 29.3 | 29.2 | 29.3 | 29.2 |
| MCHC (g/dl) | 33.4 | 33.4 | 33.6 | 33.5 |
| PLT ($\times 10^4$) | 22.9 | 23.1 | 23.0 | 23.5 |

TABLE 9

(Control)

|  | 0.5 hrs | 1 hrs | 3 hrs | 6 hrs |
|---|---|---|---|---|
| WBC ($\times 10^2$) | 47.7 | 48.2 | 49.5 | 50.3 |
| RBC ($\times 10^4$) | 542 | 541 | 546 | 547 |
| Hgb (g/dl) | 15.8 | 15.9 | 16.0 | 16.0 |
| Hct (%) | 47.9 | 47.9 | 48.8 | 49.2 |
| MCV (fl) | 87.9 | 87.9 | 88.7 | 89.3 |
| MCH (pg) | 29.3 | 29.4 | 29.2 | 29.3 |
| MCHC (g/dl) | 33.3 | 33.4 | 32.9 | 32.8 |
| PLT ($\times 10^4$) | 21.7 | 22.0 | 21.5 | 21.6 |

As clearly shown in Tables 8 and 9, data obtained with HTAD of the present invention was substantially equal to that obtained with EDTA-2K used as a control.

Subsequently, the test tubes after the blood cell count tests were centrifuged to separate plasma. The obtained plasma was subjected to biochemical tests on items of GPT, CPK, BUN, TG, UA, TCHO, TP, ALB and AMYL using an FDC-3000™ series tester (produced by Fuji Film Kabushiki Kaisha, Japan). As a control for the biochemical tests, serum and heparin-treated plasma (using Neotube™ produced by Kabushiki Kaisha Nipro, Japan) were used. The results are shown in FIGS. 3(a) to 3(c), 4(a) to 4(c) and 5(a) to 5(c).

The plasma of the HTAD-treated samples showed substantially the same behavior as the serum and heparin-treated plasma control. Therefore, it was verified that the biochemical test items can be determined with use of the HTAD of the present invention.

Example 3
CdTAD

An anticoagulant was prepared so that 22.75 mg or 2.275 mg of chondroitin sulfate (chondroitin sulfate B produced by Sigma), 1.4 mg of theophylline, 0.49 mg of adenosine and 0.05 mg dipyridamole were contained per 5-ml test tube for blood sampling.

Blood Cell Count Tests and Biochemical Tests

Blood was collected into test tubes containing chondroitin sulfate TAD (CdTAD) prepared as above and subjected to blood cell count tests. Table 10 shows mean blood cell counts of three samples.

EDTA-2K (Venoject II™ produced by Terumo), 5 mg, was used as a control for the blood cell count tests. The results are also shown in Table 10.

TABLE 10

|  | CdTAD 22.75 mg | CdTAD 2.275 mg | Control EDTA-2K |
| --- | --- | --- | --- |
| WBC ($\times 10^2$) | 64.0 | 63.5 | 61.7 |
| RBC ($\times 10^4$) | 504 | 504 | 503 |
| Hgb (g/dl) | 15.1 | 15.1 | 15.1 |
| Hct (%) | 44.7 | 44.6 | 44.8 |
| MCV (fl) | 88.8 | 88.7 | 89.2 |
| PLT ($\times 10^4$) | 18.1 | 18.0 | 24.3 |

Data obtained with CdTAD of the present invention was substantially equal to that obtained with EDTA-2K used as a control.

Subsequently, the blood samples treated with the anticoagulant containing 22.75 mg chondroitin sulfate were centrifuged to separate plasma, which was then subjected to biochemical tests on items of GGT, GOT, ALP, LDH, CRE, TBIL and CRP in addition to the test items of Example 2, using an FDC-3000™ series tester (produced by Fuji Film Kabushiki Kaisha). As a control, serum and heparin-treated plasma (using Neotube™ produced by Kabushiki Kaisha Nipro) were used. The results are shown in FIGS. 6(a) to 11.

Figure 6A:
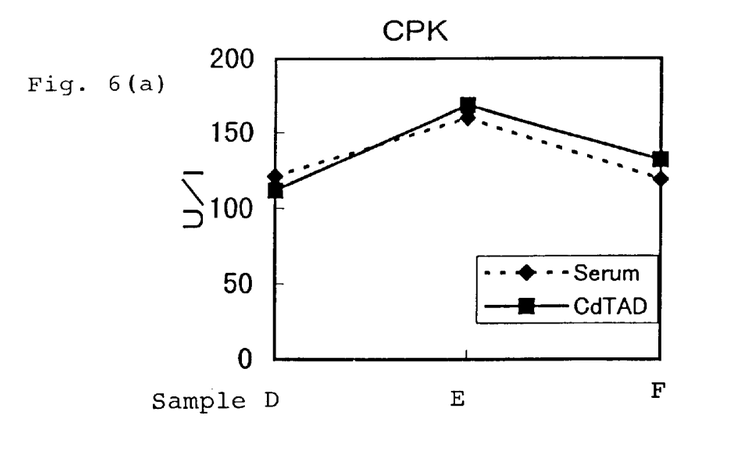
Figure 6B:
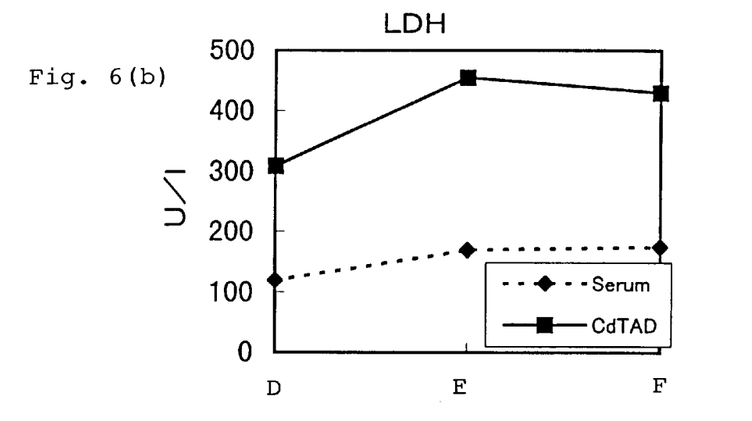
Figure 6C:
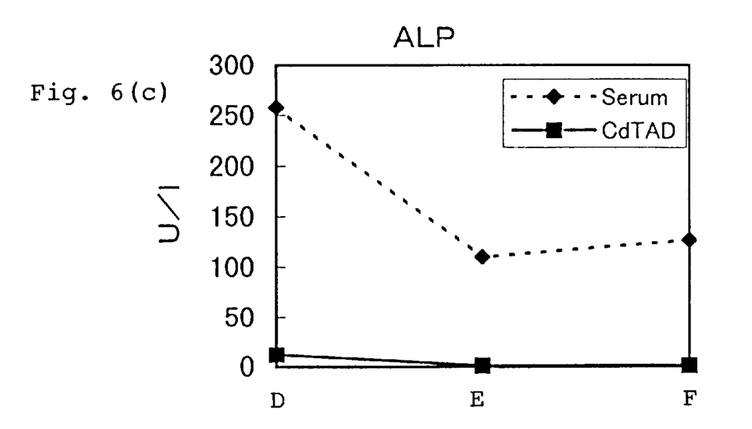
Figure 7A:
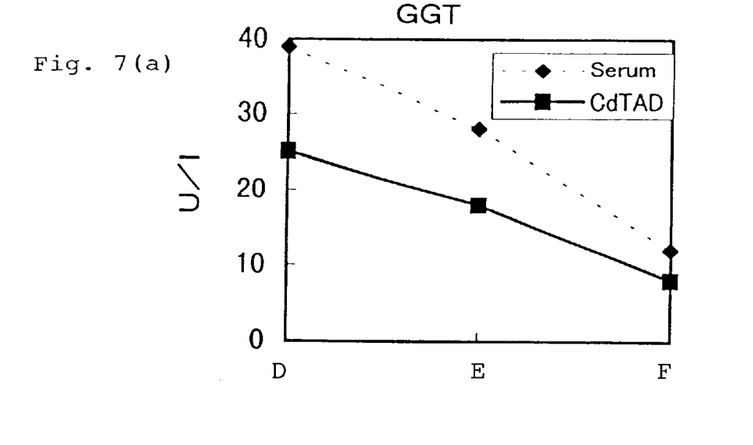
Figure 7B:
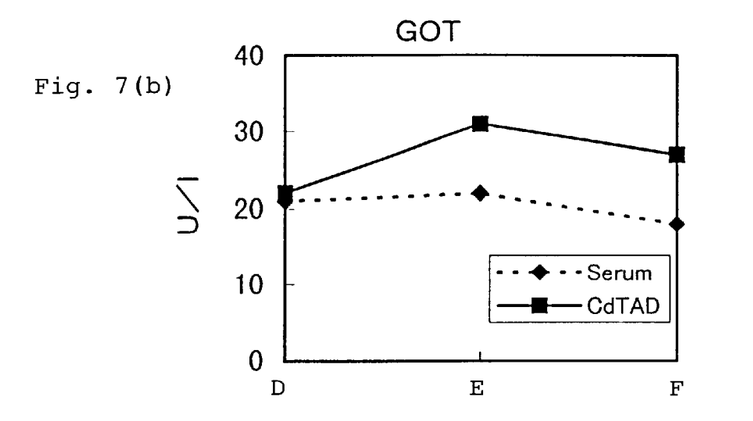
Figure 7C:
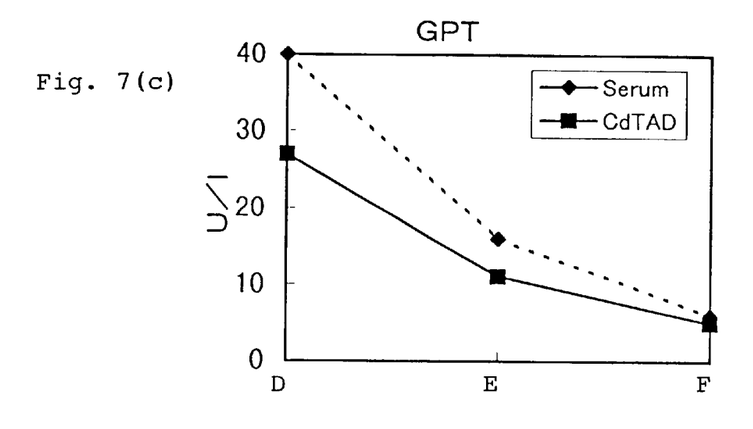
Figure 8A:
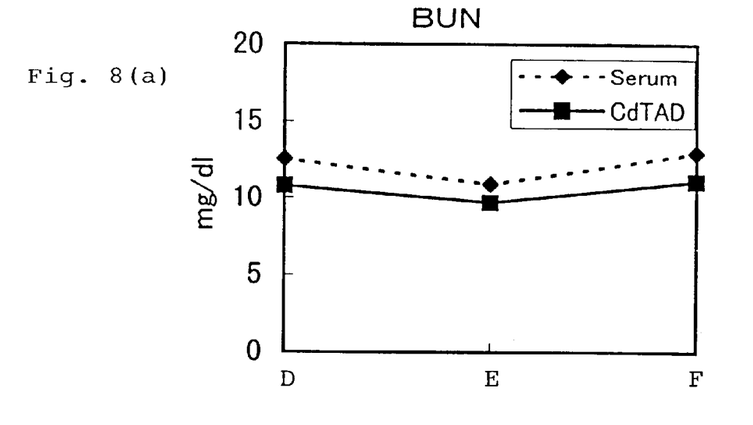
Figure 8B:
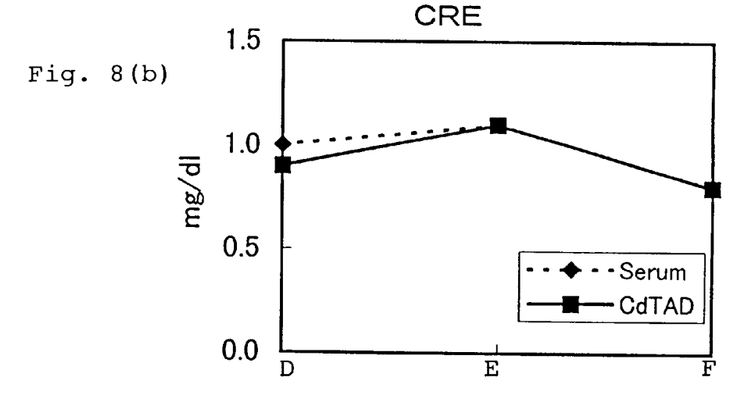
Figure 8C:
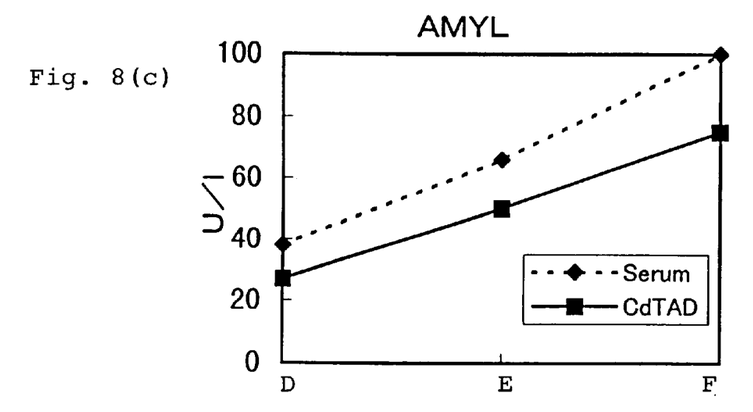
Figure 9A:
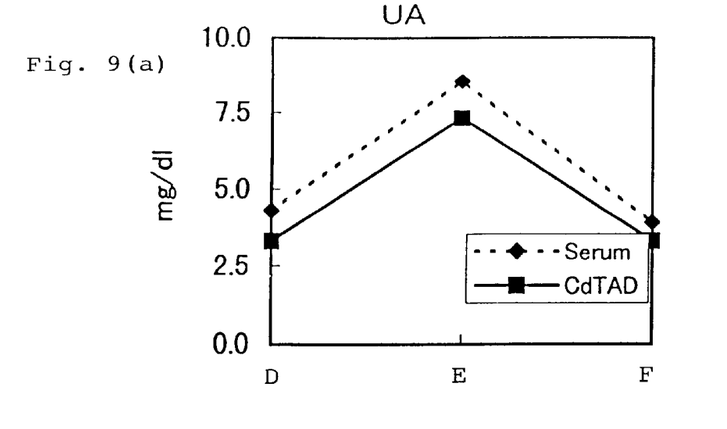
Figure 9B:
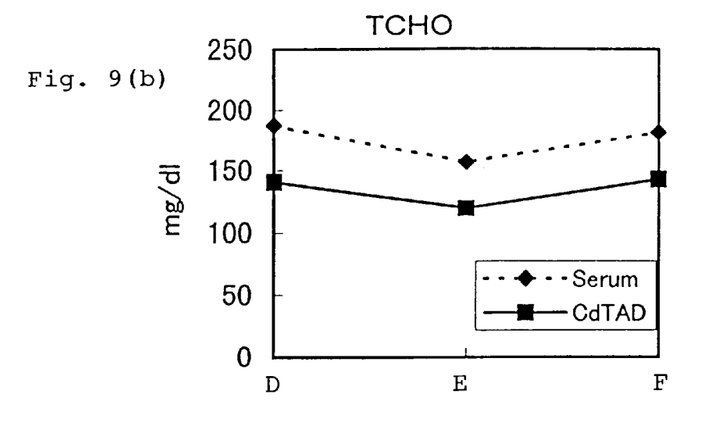
Figure 9C:
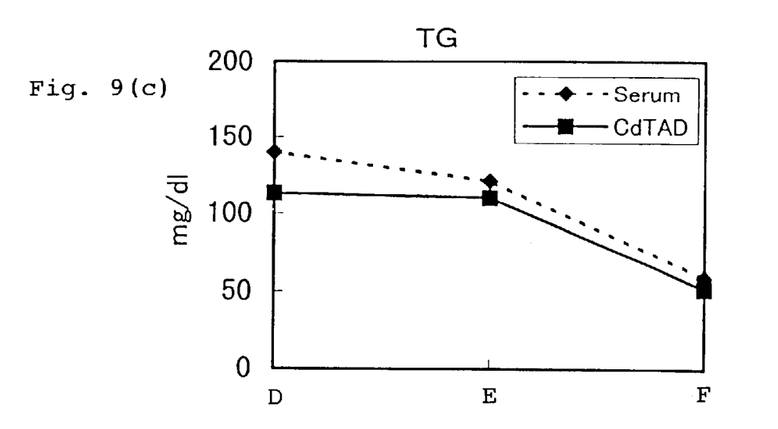
Figure 10A:
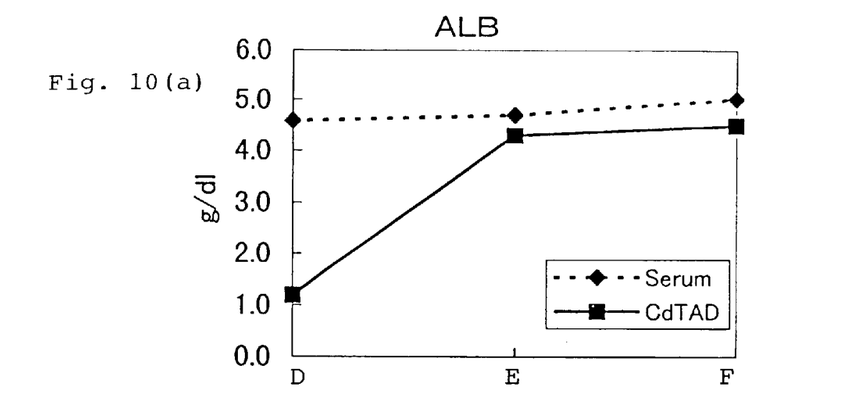
Figure 10B:
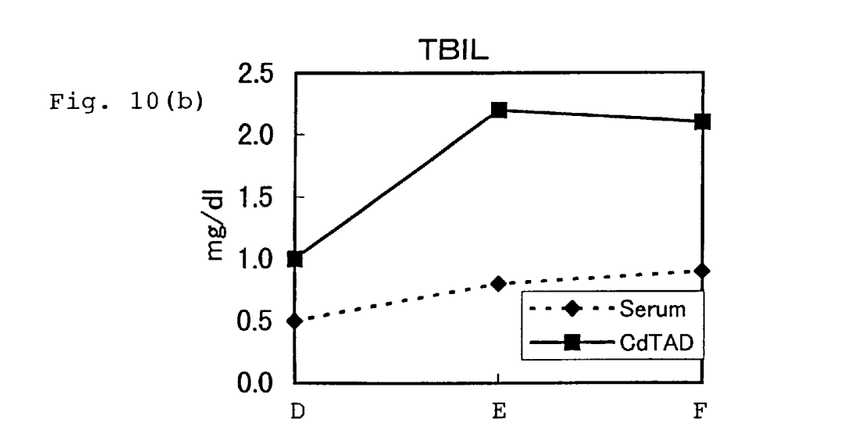
Figure 10C:
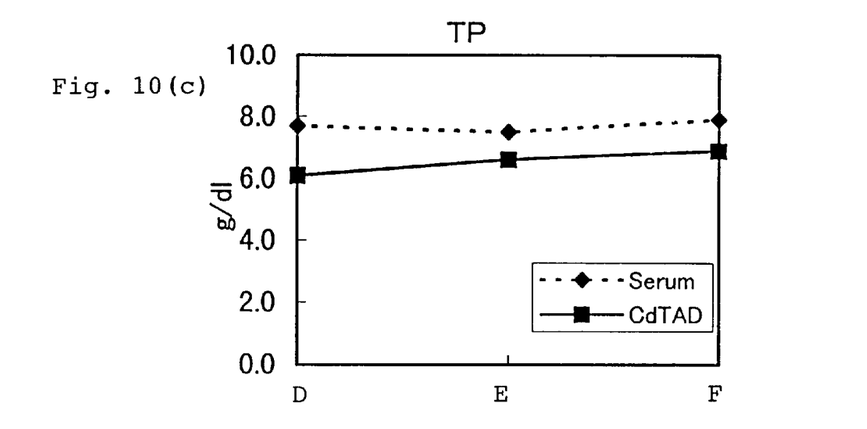
Figure 11:
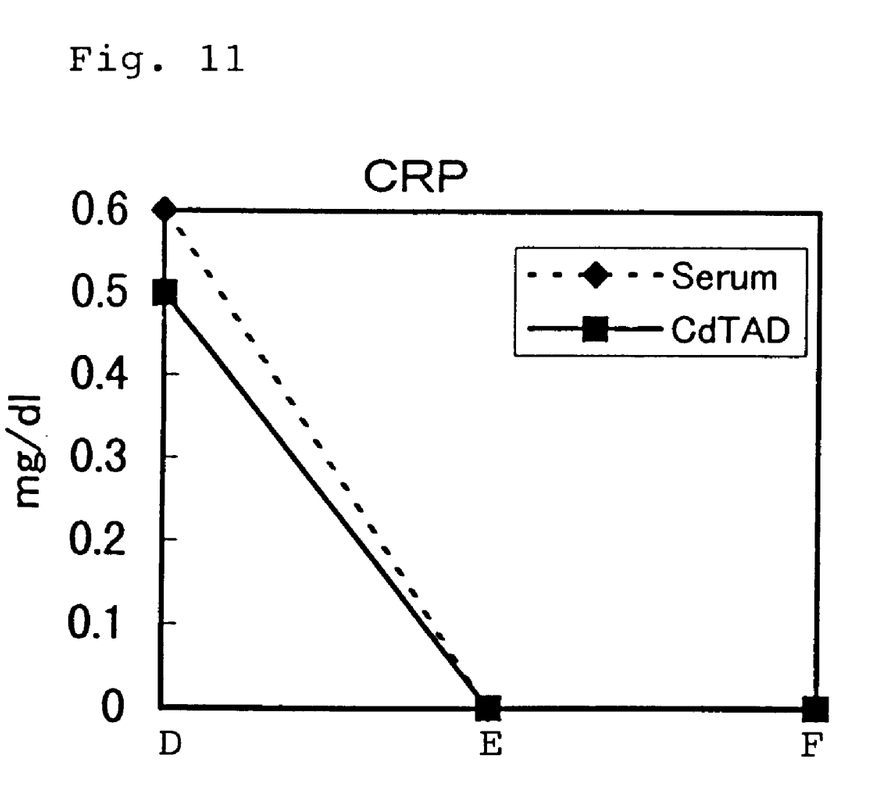
FIG. 11 is a graphical representation showing the results of biochemical tests in the case where chondroitin sulfate is used as a thrombin inhibitor of the present invention, as compared with a control.

The plasma of the CdTAD-treated samples showed substantially the same behavior as the serum control. Therefore, it was verified that CdTAD of the present invention can be used for the biochemical tests.

According to the present invention, since blood cell count tests and coagulation tests or blood cell count tests and biochemical tests can be conducted with use of the same anticoagulant, the number of necessary test tubes for blood sampling can be reduced. Accordingly the collection of blood can be preformed with less time and effort at reduced costs and also a patient will be less burdened.

Further, since blood cell count tests and coagulation tests or blood cell count tests and biochemical test can be conducted with use of only one test tube for blood sampling, it is possible to connect automatic analyzers via a sample conveyor system to establish systematization.

Since the EDTA salts are not used in the present invention, it is possible to prevent the pseudothrombocytopenia and also to prevent platelets from expanding as time passes, so that the size of platelets can be maintained stably at their original size.

Also it is possible to conduct an accurate blood cell counting without agglutinating even with regard to a sample which may have cold agglutination, by use of the anticoagulant of the present invention.

What is claimed is:

1. A hemanalysis method comprising:

adding, to a blood sample, a dry anticoagulant comprising at least two kinds of antiplatelet agents selected from the group consisting of theophyllines, adenosines and dipyridamoles, as well as citric acid, an alkali metal salt thereof or a mixture of citric acid and an alkali metal salt thereof, counting at least two kinds of blood cells selected from the group consisting of leukocytes, erythrocytes and platelets in the blood sample, and carrying out a blood coagulation test to determine prothrombin time or fibrinogen.

* * * * *